(12) United States Patent
Creus

(10) Patent No.: US 10,092,643 B2
(45) Date of Patent: Oct. 9, 2018

(54) PROPHYLACTIC AND IMMUNOMODULATORY COMPOSITIONS AND USES

(75) Inventor: Marc Creus, Geneva (CH)

(73) Assignee: Kherion Technology Limited

(*) Notice: Subject to any disclaimer, the term of this patent is extended or adjusted under 35 U.S.C. 154(b) by 2226 days.

(21) Appl. No.: 11/994,050

(22) PCT Filed: Jun. 30, 2006

(86) PCT No.: PCT/GB2006/002424
§ 371 (c)(1),
(2), (4) Date: Jul. 15, 2010

(87) PCT Pub. No.: WO2007/003904
PCT Pub. Date: Jan. 11, 2007

(65) Prior Publication Data
US 2010/0278903 A1    Nov. 4, 2010

(30) Foreign Application Priority Data
Jun. 30, 2005 (GB) .................................. 0513431.7

(51) Int. Cl.
*A61K 39/39* (2006.01)
*A61K 39/00* (2006.01)

(52) U.S. Cl.
CPC .... *A61K 39/39* (2013.01); *A61K 2039/55544* (2013.01); *A61K 2039/55555* (2013.01)

(58) Field of Classification Search
None
See application file for complete search history.

(56) References Cited

U.S. PATENT DOCUMENTS

| | | | |
|---|---|---|---|
| 5,256,641 A * | 10/1993 | Yatvin et al. .................. | 514/2.3 |
| 5,391,800 A | 2/1995 | Igarashi et al. | |
| 5,430,169 A | 7/1995 | Boumendjel et al. | |
| 5,897,860 A | 4/1999 | Kim et al. | |
| 6,147,118 A | 11/2000 | Lambers et al. | |
| 6,239,297 B1 | 5/2001 | Takesako et al. | |
| 6,248,329 B1 * | 6/2001 | Chandrashekar et al. ................... | 424/191.1 |
| 6,280,774 B1 | 8/2001 | Rang | |
| 6,667,025 B2 | 12/2003 | Chiba et al. | |
| 8,377,910 B2 | 2/2013 | Fraziano et al. | |
| 2002/0049183 A1 * | 4/2002 | Yedgar ............. A61K 47/48053 | 514/54 |
| 2004/0067910 A1 | 4/2004 | Msika et al. | |
| 2004/0092603 A1 | 5/2004 | Chiba et al. | |
| 2005/0009757 A1 * | 1/2005 | Fraziano .............. A61K 31/047 | 514/25 |
| 2006/0134182 A1 | 6/2006 | Nieuwenhuizen | |
| 2006/0135786 A1 * | 6/2006 | Saha ..................... C07C 237/04 | 548/341.1 |
| 2006/0252717 A1 | 11/2006 | Barenholz et al. | |
| 2008/0090913 A1 | 4/2008 | Braxmeier et al. | |

FOREIGN PATENT DOCUMENTS

| | | |
|---|---|---|
| CA | 2323887 | 9/1999 |
| DE | 19810999 | 9/1999 |
| EP | 0 321 287 | 6/1989 |
| WO | WO98/52575 | 11/1998 |
| WO | WO2002/048709 | 6/2002 |
| WO | WO02/060405 | 8/2002 |
| WO | WO02/064616 | 8/2002 |
| WO | WO03/045365 | 6/2003 |
| WO | WO03/097028 | 11/2003 |
| WO | WO04/024673 | 3/2004 |
| WO | WO2004/028521 | 4/2004 |
| WO | WO2004/096752 | 11/2004 |
| WO | WO04/110496 | 12/2004 |
| WO | WO/2004/110496 | * 12/2004 |

OTHER PUBLICATIONS

Bowie et al (Science, 1990, 247:1306-1310.*
Spiegel et al, The Journal of Membrane Biology, 146:225-237, 1995.*
Wang et al Biochem J. 324:481-488, 1997.*
Vogel, Annals of the NY Academy of Sciences 754:153-60, 1995.*
Mandala et al, Science 296:346-349, 2002.*
Brinkmann et al (The Journal of Biological Chemistry, 277(24):21453-57, 2002).*
webmd.com/rheumatoid-arthritis/guide/the-causes-of-rheumatoid-arthritis; one page.*
Skurkovich et al (Expert Review of Clinical Immunology, May 2005, 1(1):11-25.*
Garg et al. 2004 (Sphingosine 1 Phosphate Induces Antimicrobial Activity in Both in vitro and in vivo; JID 189:2129-2138).*
Hla 2004 (Physiological and phathological actions of sphingosine 1-phosphate; Seminars in Cell & Developmental Biology 15:513-520).*
Goetzl et al. 2004 (Sphingosine 1-Phosphate and Its G-protein-coupled receptors constitute a multifunctional immunoregulatory system; J of Cell Biochem 92:1104-1114).*
Sherer et al. 2006 (Mechanisms of Disease: Atherosclerosis in Autoimmune Disease; Nature Clinical Practice Rheumatology vol. 2(2): 99-106).*
Mandala et al. 2002 (Alteration of lymphocyte trafficking by Sphingosine-1-Phosphate Receptor Agonists; Science 296:346-349).*

(Continued)

*Primary Examiner* — Mary Maille Lyons
(74) *Attorney, Agent, or Firm* — Fish & Richardson P.C.

(57) ABSTRACT

Provided is use of a sphingosine compound, or a derivative of a sphingosine compound, in the manufacture of a vaccine effective in the treatment and prevention of an infectious disease and treatment and/or prevention of an autoimmune disease. Also provided is use of a sphingosine compound, or a derivative of a sphingosine compound, in the manufacture of an immunomodulation medicament effective in the prevention of infectious disease and treatment and/or prevention of an autoimmune disease.

10 Claims, No Drawings

(56) References Cited

OTHER PUBLICATIONS

Greenstein 2003 (Is Crohn's Disease Caused by a *Mycobacterium*? Comparisons with leprosy, tuberculosis, and Johne's Disease; The Lancet Infectious Diseases 3:507-514).*
Garg et al. 2004 (Sphingosine 1 Phosphate Induces Antimicrobial Activity in vitro and in vivo; JID 189:2129-2138).*
Rook et al. 1992 (Slow bacterial infections or autoimmunity; Immunology.*
Garg et al. 2004 (Sphingosine 1 Phosphate Induces Antimicrobial Activity in vitro and in vivo; JID 189:2129-2138 (Year: 2004).*
Rook et al. 1992 (Slow bacterial infections or autoimmunity; Immunology Today 13(5):160-164). (Year: 1992).*
Abbott, M., et al., "Haemochromatosis Presenting with a Double Yersinia Infection," J. Infection 1986;13:143-145.
Akaki, T. et al, "Comparative roles of free fatty acids with reactive nitrogen intermediates and reactive oxygen intermediates in expression of the anti-microbial activity of macrophages against *Mycobacterium tuberculosis*", Clin. Exp. Immunol., 121, 302-310, 2000.
Ben-Av, P., et al., "Distinct mechanisms of phospholipase D activation and attenuation utilized by different mitogens in N1H-3T3 fibroblasts," Eur. J. Biochem. 1993;215:455-463.
Bhaskaram, P., "Immunobiology of mild micronutrient deficiencies," Brit. J. Nutr. 2001;85:S75-S80.
Eswarappa, S. M., et al., "Division of the *Salmonella*-Containing Vacuole and Depletion of Acidic Lysosomes in *Salmonella*-Infected Host Cells Are Novel Strategies of *Salmonella enteric* to Avoid Lysosomes," Infection Immun. 2010;78(I):68-79.
Lamothe, J., et al., "Burkholderia cenocepacia-induced delay of acidification and phagolysosomal fusion in cystic transmembrane conductance regulator (CFTR)-defective macrophages," Microbiol. 2008;154:3825-3834. fibrosis.
Lin, M., et al., "Role of iron in NF-kappa B activation and cytokine gene expression by rat hepatic macrophages," Am. J. Physiol.-Gastr. L. 1997;35:G1355-G1364.
Nathan, C, et al., "Reactive oxygen and nitrogen intermediates in the relationship between mammalian hosts and microbial pathogens," PNAS 2000;97(16):8841-8848.
Ohanian, J. etal., "Sphingolipids in Mammalian Cell Signalling", CMLS Cellular and Molecular Life Sciences, 58, 2053-2068, 2001.
Remer, K.A.. et al., "Nitric Oxide is Protective in Listeric Meningoencephalitis of Rats", Infection and Immunity, 4086-4093, Jun. 2001.
Videla, L.A., et al., "Oxidative stress-mediated hepatotoxicity of iron and copper: Role of Kupffer cells," Biometals 2003;16:103-111.
Tillett & Sherry, J. Clin. Invest., 1949:173-190.
Samy et al., J. Immunol. Nov. 1, 2007; 179(9): 5644-8.
Helms, Eur J Lipid Sci. Technol. 108 (2006) 895-897.
Pankova-Kholmyansky & Flescher, Chemotherapy (2006) 52: 205-209.
Hanada et al., Jpn. J. Infect. Dis. (2005) 58: 131-148.
McQuiston et al., Mini-Reviews in Medicinal Chemistry (2006); 6:671-680.
McQuiston, T.; Luberto, C.; Del Poeta, M. Microbiology-Sgm (2011) 157, 1416-1427.
Deretic, V.; Vergne, I.; Chua, J.; Master, S.; Singh, S. B.; Fazio, J. A.; Kyei, G. Cellular Microbiology 2004, 6, 999-1009.
Vergne, I.; Singh, S.; Roberts, E.; Kyei, G.; Master, S.; Harris, J.; de Haro, S.; Naylor, J.; Davis, A.; Delgado, M.; Deretic, V. Autophagy 2006, 2, 175-178.
Levine, B.; Deretic, V. Nature Reviews Immunology 2007, 7, 767-777.
Kyei, G. B.; Dinkins, C.; Davis, A. S.; Roberts, E.; Singh, S. B.; Dong, C. S.; Wu, L.; Kominami, E.; Ueno, T.; Yamamoto, A.; Federico, M.; Panganiban, A.; Vergne, I.; Deretic, V. Journal of Cell Biology 2009, 186, 255-268.
Gutierrez, M. G.; Master, S. S.; Singh, S. B.; Taylor, G. A.; Colombo, M. I.; Deretic, V. Cell 2004, 119, 753-766.

Office Action from co-pending U.S. Appl. No. 13/743,516 dated Dec. 5, 2013.
Bendelac, A., Rivera, M.N., Park, S.-H., and Roark, J.H. (1997). Mouse CD1-Specific NK1 T Cells: Development, Specificity, and Function. Annu. Rev. Immunol. 15, 535-562.
Berkers, C.R., and Ovaa, H. (2005). Immunotherapeutic potential for ceramide-based activators of iNKT cells. Trends Pharmacol. Sci. 26, 252-257.
Blaise, G.A., Gauvin, D., Gangal, M., and Authier, S. (2005). Nitric oxide, cell signaling and cell death. Toxicology 208, 177-192.
Chackerian, A., Alt, J., Perera, V., and Behar, S.M. (2002). Activation of NKT Cells Protects Mice from Tuberculosis. Infect. Immun. 70, 6302-6309.
Chang, D.H., Osman, K., Connolly, J., Kukreja, A., Krasovsky, J., Pack, M., Hutchinson, A., Geller, M., Liu, N., Annable, R., et al. (2005). Sustained expansion of NKT cells and antigen-specific T cells after injection of α-galactosyl-ceramide loaded mature dendritic cells in cancer patients. J. Exp. Med. 201, 1503-1517.
Chen, G., Schmieg, J., Tsuji, M., and Franck, R.W. (2004). Efficient Synthesis of α-C-Galactosyl Ceramide Immunostimulants: Use of Ethylene-Promoted Olefin Cross-Metathesis. Org. Lett. 6, 4077-4080.
Chiba, A., Kaieda, S., Oki, S., Yamamura, T., and Miyake, S. (2005). The involvement of Vα14 natural killer T cells in the pathogenesis of arthritis in murine models. Arthritis Rheum. 52, 1941-1948.
Chu, C.-Q., Wittmer, S., and Dalton, D.K. (2000). Failure to Suppress the Expansion of the Activated Cd4 T Cell Population in Interferon γ-Deficient Mice Leads to Exacerbation of Experimental Autoimmune Encephalomyelitis. J. Exp. Med. 192, 123-128.
Crowe, N.Y., Smyth, M.J., and Godfrey, D.I. (2002). A Critical Role for Natural Killer T Cells in Immunosurveillance of Methylcholanthrene-induced Sarcomas. J. Exp. Med. 196, 119-127.
Cua, D.J., Sherlock, J., Chen, Y., Murphy, C.A., Joyce, B., Seymour, B., Lucian, L., To, W., Kwan, S., Churakova, T., et al. (2003). Interleukin-23 rather than interleukin-12 is the critical cytokine for autoimmune inflammation of the brain. Nature 421, 744-748.
Dalton, D.K., Haynes, L., Chu, C.-Q., Swain, S.L., and Wittmer, S. (2000). Interferon γ Eliminates Responding Cd4 T Cells during *Mycobacterial* Infection by Inducing Apoptosis of Activated Cd4 T Cells. J. Exp. Med. 192, 117-122.
Dhakshinamoorthy, S., and Porter, A.G. (2004). Nitric Oxide-induced Transcriptional Up-regulation of Protective Genes by Nrf2 via the Antioxidant Response Element Counteracts Apoptosis of Neuroblastoma Cells. J. Biol. Chem. 279, 20096-20107.
Ferber, I.A., Brocke, S., Taylor-Edwards, C., Ridgway, W., Dinisco, C., Steinman, L., Dalton, D., and Fathman, C.G. (1996). Mice with a disrupted IFN-gamma gene are susceptible to the induction of experimental autoimmune encephalomyelitis (EAE). J. Immunol. 156, 5-7.
Fuji, N., Ueda, Y., Fujiwara, H., Itoh, T., Yoshimura, T., and Yamagishi, H. (2000). Antitumor Effect of α-Galactosylceramide (KRN7000) on Spontaneous Hepatic Metastases Requires Endogenous Interleukin 12 in the Liver. Clin. Cancer Res. 6, 3380-3387.
Fujii, S., Shimizu, K., Smith, C., Bonifaz, L., and Steinman, R.M. (2003). Activation of Natural Killer T Cells by α-Galactosylceramide Rapidly Induces the Full Maturation of Dendritic Cells In Vivo and Thereby Acts as an Adjuvant for Combined CD4 and CD8 T Cell Immunity to a Coadministered Protein. J. Exp. Med. 198, 267-279.
Fujio, M., Wu, D., Garcia-Navarro, R., Ho, D.D., Tsuji, M., and Wong, C.-H. (2006). Structure-Based Discovery of Glycolipids for CD1d-Mediated NKT Cell Activation: Tuning the Adjuvant versus Immunosuppression Activity. J. Am. Chem. Soc. 128, 9022-9023.
Giaccone, G., Punt, C.J.A., Ando, Y., Ruijter, R., Nishi, N., Peters, M., Blomberg, B.M.E. von, Scheper, R.J., Vliet, H.J.J. van der, Eertwegh, A.J.M. van den, et al. (2002). A Phase I Study of the Natural Killer T-Cell Ligand α-Galactosylceramide (KRN7000) in Patients with Solid Tumors. Clin. Cancer Res. 8, 3702-3709.
Goff, R.D., Gao, Y., Mattner, J., Zhou, D., Yin, N., Cantu, C., Teyton, L., Bendelac, A., and Savage, P.B. (2004). Effects of Lipid Chain Lengths in α-Galactosylceramides on Cytokine Release by Natural Killer T Cells. J. Am. Chem. Soc. 126, 13602-13603.
Gonzalez-Aseguinolaza, G., Kaer, L.V., Bergmann, C.C., Wilson, J.M., Schmieg, J., Kronenberg, M., Nakayama, T., Taniguchi, M.,

(56) References Cited

OTHER PUBLICATIONS

Koezuka, Y., and Tsuji, M. (2002). Natural Killer T Cell Ligand α-Galactosylceramide Enhances Protective Immunity Induced by Malaria Vaccines. J. Exp. Med. 195, 617-624.

Gonzalez-Aseguinolaza, G., Oliveira, C. de, Tomaska, M., Hong, S., Bruna-Romero, O., Nakayama, T., Taniguchi, M., Bendelac, A., Kaer, L.V., Koezuka, Y., et al. (2000). α-Galactosylceramide-activated Vα14 natural killer T cells mediate protection against murine malaria. Proc. Natl. Acad. Sci. 97, 8461-8466.

Guo, S., Hakimi, M.-A., Baillat, D., Chen, X., Farber, M.J., Klein-Szanto, A.J.P., Cooch, N.S., Godwin, A.K., and Shiekhattar, R. (2005). Linking Transcriptional Elongation and Messenger RNA Export to Metastatic Breast Cancers. Cancer Res. 65, 3011-3016.

Harrington, L.E., Hatton, R.D., Mangan, P.R., Turner, H., Murphy, T.L., Murphy, K.M., and Weaver, C.T. (2005). Interleukin 17—producing CD4+ effector T cells develop via a lineage distinct from the T helper type 1 and 2 lineages. Nat. Immunol. 6, 1123-1132.

Harris, E.D. (1990). Rheumatoid Arthritis. N. Engl. J. Med. 322, 1277-1289.

Hermans, I.F., Silk, J.D., Gileadi, U., Salio, M., Mathew, B., Ritter, G., Schmidt, R., Harris, A.L., Old, L., and Cerundolo, V. (2003). NKT Cells Enhance CD4+ and CD8+ T Cell Responses to Soluble Antigen In Vivo through Direct Interaction with Dendritic Cells. J. Immunol. 171, 5140-5147.

Hong, S., Wilson, M.T., Serizawa, I., Wu, L., Singh, N., Naidenko, O.V., Miura, T., Haba, T., Scherer, D.C., Wei, J., et al. (2001). The natural killer T-cell ligand α-galactosylceramide prevents autoimmune diabetes in non-obese diabetic mice. Nat. Med. 7, 1052-1056.

Ishikawa, A., Motohashi, S., Ishikawa, E., Fuchida, H., Higashino, K., Otsuji, M., Iizasa, T., Nakayama, T., Taniguchi, M., and Fujisawa, T. (2005). A Phase I Study of α-Galactosylceramide (KRN7000)—Pulsed Dendritic Cells in Patients with Advanced and Recurrent Non-Small Cell Lung Cancer. Clin. Cancer Res. 11, 1910-1917.

Jahng, A.W., Maricic, I., Pedersen, B., Burdin, N., Naidenko, O., Kronenberg, M., Koezuka, Y., and Kumar, V. (2001). Activation of natural killer T cells potentiates or prevents experimental autoimmune encephalomyelitis. J. Exp. Med. 194, 1789-1799.

Kaer, L.V. (2005). α-Galactosylceramide therapy for autoimmune diseases: prospects and obstacles. Nat. Rev. Immunol. 5, 31-42.

Kakimi, K. Guidotti, L.G., Koezuka, Y., and Chisari, F.V. (2000). Natural Killer T Cell Activation Inhibits Hepatitis B Virus Replication in Vivo. J. Exp. Med. 192, 921-930.

Kawakami, K., Kinjo, Y., Yara, S., Koguchi, Y., Uezu, K., Nakayama, T., Taniguchi, M., and Saito, A. (2001a). Activation of Vα14+ Natural Killer T Cells by α-Galactosylceramide Results in Development of Th1 Response and Local Host Resistance in Mice Infected with Cryptococcus neoformans. Infect. Immun. 69, 213-220.

Kawakami, K., Kinjo, Y., Yara, S., Uezu, K., Koguchi, Y., Tohyama, M., Azuma, M., Takeda, K., Akira, S., and Saito, A. (2001b). Enhanced Gamma Interferon Production through Activation of Valpha 14+ Natural Killer T Cells by alpha-Galactosylceramide in Interleukin-18-Deficient Mice with Systemic Cryptococcosis. Infect. Immun. 69, 6643-6650.

Kawano, T., Cui, J., Koezuka, Y., Toura, I., Kaneko, Y., Sato, H., Kondo, E., Harada, M., Koseki, H., Nakayama, T., et al. (1998). Natural killer-like nonspecific tumor cell lysis mediated by specific ligand-activated Vα14 NKT cells. Proc. Natl. Acad. Sci. 95, 5690-5693.

Kim, H.Y. Kim, H.J., Min H.S., Kim, S., Park, W.S., Park, S H., and Chung, D.H. (2005). NKT cells promote antibody-induced joint inflammation by suppressing transforming growth factor β1 production. J. Exp. Med. 201, 41-47.

Kim, S. and Chung, D.H. (2006). FcγRIII engagement provides activating signals to NKT cells in antibody-induced joint inflammation. J. Clin. Invest. 116, 2484-2492.

Kinjo, Y., Wu, D., Kim, G., Xing, G.-W., Poles, M.A., Ho, D.D., Tsuji, M., Kawahara, K., Wong, C.-H., and Kronenberg, M. (2005). Recognition of bacterial glycosphingolipids by natural killer T cells. Nature 434, 520-525.

Kojo, S., Adachi, Y., Keino, H., Taniguchi, M., and Sumida, T. (2001). Dysfunction of T cell receptor AV24AJ18+,BV11+ double-negative regulatory natural killer T cells in autoimmune diseases. Arthritis Rheum. 44, 1127-1138.

Komiyama, Y., Nakae, S., Matsuki, T., Nambu, A., Ishigame, H., Kakuta, S., Sudo, K., and Iwakura, Y. (2006). IL-17 Plays an Important Role in the Development of Experimental Autoimmune Encephalomyelitis. J. Immunol. 177, 566-573.

Kronenberg, M. (2005). Toward an Understanding of NKT Cell Biology: Progress and Paradoxes. Annu. Rev. Immunol. 23, 877-900.

Kronenberg, M., and Gapin, L. (2002). The unconventional lifestyle of NKT cells. Nat. Rev. Immunol. 2, 557-568.

Li, Y. Wang, X. Zhang, X. and Goodrich, D.W. (2005). Human hHpr1/p84/Thoc1 Regulates Transcriptional Elongation and Physically Links RNA Polymerase II and RNA Processing Factors. Mol. Cell. Biol. 25, 4023-4033.

Lublin, F.D., and Reingold, S.C. (1996). Defining the clinical course of multiple sclerosis: results of an international survey. National Multiple Sclerosis Society (USA) Advisory Committee on Clinical Trials of New Agents in Multiple Sclerosis. Neurology 46, 907-911.

Luross, J.A., and Williams, N.A. (2001). The genetic and immunopathological processes underlying collagen-induced arthritis. Immunology 103, 407-416.

Maeda, T., Keino, H., Asahara, H., Taniguchi, M., Nishioka, K., and Sumida, T. (1999). Decreased TCR AV24AJ18+ double-negative T cells in rheumatoid synovium. Rheumatology 38, 186-188.

Marburg, O. (1906). Die sogenannte akute multiple Sklerose (Jahrb Psychiatrie).

Miyamoto, K. Miyake, S., and Yamamura, T. (2001). A synthetic glycolipid prevents autoimmune encephalomyelitis by inducing TH2 bias of natural killer T cells. Nature 413, 531-534.

Murphy, C.A., Langrish, C.L., Chen, Y., Blumenschein, W., McClanahan, T., Kastelein, R.A., Sedgwick, J.D., and Cua, D.J. (2003). Divergent Pro- and Antiinflammatory Roles for IL-23 and IL-12 in Joint Autoimmune Inflammation. J. Exp. Med. 198, 1951-1957.

Nakae, S., Nambu, A., Sudo, K., and Iwakura, Y. (2003). Suppression of Immune Induction of Collagen-Induced Arthritis in IL-17-Deficient Mice. J. Immunol. 171, 6173-6177.

Nakagawa, R., Serizawa, I., Motoki, K., Sato, M., Ueno, H., Iijima, R., Nakamura, H., Shimosaka, A., and Koezuka, Y. (2001). Antitumor Activity of α-Galactosylceramide, KRN7000, in Mice With the Melanoma B16 Hepatic Metastasis and Immunohistological Study of Tumor Infiltrating Cells. Oncol. Res. Featur. Preclin. Clin. Cancer Ther. 12, 51-58.

Nakui, M., Iwakabe, K., Ohta, A., Sekimoto, M., Sato, M., Makuuchi, H., Kawano, T., Taniguchi, M., and Nishimura, T. (1999). Natural killer T cell ligand alpha-galactosylceramide inhibited lymph node metastasis of highly metastatic melanoma cells. Jpn. J. Cancer Res. Gann 90, 801-804.

Nakui, M., Ohta, A., Sekimoto, M., Sato, M., Iwakabe, K., Yahata, T., Kitamura, H., Koda, T., Kawano, T., Makuuchi, H., et al. (2000). Potentiation of antitumor effect of NKT cell ligand, alpha-galactosylceramide by combination with IL-12 on lung metastasis of malignant melanoma cells. Clin. Exp. Metastasis 18, 147-153.

Nieda, M. (2004). Therapeutic activation of V 24+V 11+ NKT cells in human subjects results in highly coordinated secondary activation of acquired and innate immunity. Blood 103, 383-389.

Ohnishi, Y., Tsutsumi, A., Goto, D., Itoh, S., Matsumoto, I., Taniguchi, M., and Sumida, T. (2005). TCR Vα14+ natural killer T cells function as effector T cells in mice with collagen-induced arthritis. Clin. Exp. Immunol. 141, 47-53.

Oki, S., Chiba, A., Yamamura, T., and Miyake, S. (2004). The clinical implication and molecular mechanism of preferential IL-4 production by modified glycolipid-stimulated NKT cells. J. Clin. Invest. 113, 1631-1640.

Parekh, V.V. (2005). Glycolipid antigen induces long-term natural killer T cell anergy in mice. J. Clin. Invest. 115, 2572-2583.

Rodrigues, E.G., Zavala, F., Eichinger, D., Wilson, J.M., and Tsuji, M. (1997). Single immunizing dose of recombinant adenovirus efficiently induces CD8+ T cell-mediated protective immunity against malaria. J. Immunol. 158, 1268-1274.

(56) References Cited

OTHER PUBLICATIONS

Rodrigues, M.M., Cordey, A.-S., Arreaza, G., Corradin, G., Romero, P., Maryanski, J.L., Nussenzweig, R.S., and Zavala, F. (1991). CD8+ cytolytic T cell clones derived against the Plasmodium yoelii circumsporozoite protein protect against malaria. Int. Immunol. 3, 579-585.

Romero, P., Maryanski, J.L., Corradin, G., Nussenzweig, R.S., Nussenzweig, V., and Zavala, F. (1989). Cloned cytotoxic T cells recognize an epitope in the circumsporozoite protein and protect against malaria. Nature 341, 323-326.

Schmieg, J., Yang, G., Franck, R.W., and Tsuji, M. (2003). Superior Protection against Malaria and Melanoma Metastases by a C-glycoside Analogue of the Natural Killer T Cell Ligand α-Galactosylceramide. J. Exp. Med. 198, 1631-1641.

Schmieg, J., Yang, G., Franck, R.W., Rooijen, N.V., and Tsuji, M. (2005). Glycolipid presentation to natural killer T cells differs in an organ-dependent fashion. Proc. Natl. Acad. Sci. U. S. A. 102, 1127-1132.

Schofield, L., Villaquiran, J., Ferreira, A., Schellekens, H., Nussenzweig, R., and Nussenzweig, V. (1987). γ Interferon, CD8+ T cells and antibodies required for immunity to malaria sporozoites. Nature 330, 664-666.

Sharif, S., Arreaza, G.A., Zucker, P., Mi, Q.-S., Sondhi, J., Naidenko, O.V., Kronenberg, M., Koezuka, Y., Delovitch, T.L., Gombert, J.-M., et al. (2001). Activation of natural killer T cells by α-galactosylceramide treatment prevents the onset and recurrence of autoimmune Type 1 diabetes. Nat. Med. 7, 1057-1062.

Shimazu, R., Akashi, S., Ogata, H., Nagai, Y., Fukudome, K., Miyake, K., and Kimoto, M. (1999). MD-2, a Molecule that Confers Lipopolysaccharide Responsiveness on Toll-like Receptor 4. J. Exp. Med. 189, 1777-1782.

Silk, J.D., Hermans, I.F., Gileadi, U., Chong, T.W., Shepherd, D., Salio, M., Mathew, B., Schmidt, R.R., Lunt, S.J., Williams, K.J., et al. (2004). Utilizing the adjuvant properties of CD1d-dependent NK T cells in T cell-mediated immunotherapy. J. Clin. Invest. 114, 1800-1811.

Singh, A.K., Wilson, M.T., Hong, S., Olivares-Villagómez, D., Du, C., Stanic, A.K., Joyce, S., Sriram, S., Koezuka, Y., and Kaer, L.V. (2001). Natural Killer T Cell Activation Protects Mice Against Experimental Autoimmune Encephalomyelitis. J. Exp. Med. 194, 1801-1811.

Smyth, M.J., Thia, K.Y.T., Street, S.E.A., Cretney, E., Trapani, J.A., Taniguchi, M., Kawano, T., Pelikan, S.B., Crowe, N.Y., and Godfrey, D.I. (2000). Differential Tumor Surveillance by Natural Killer (Nk) and Nkt Cells. J. Exp. Med. 191, 661-668.

Sumida, T., Maeda, T., Taniguchi, M., Nishioka, K., and Stohl, W. (1998). TCR AV24 gene expression in double negative T cells in systemic lupus erythematosus. Lupus 7, 565-568.

Sumida, T., Sakamoto, A., Murata, H., Makino, Y., Takahashi, H., Yoshida, S., Nishioka, K., Iwamoto, I., and Taniguchi, M. (1995). Selective reduction of T cells bearing invariant V alpha 24J alpha Q antigen receptor in patients with systemic sclerosis. J. Exp. Med. 182, 1163-1168.

Tomioka, H. (2004). Adjunctive immunotherapy of mycobacterial infections. Curr. Pharm. Des. 10, 3297-3312.

Umansky, V., and Schirrmacher, V. (2001). Nitric oxide-induced apoptosis in tumor cells. Adv. Cancer Res. 82, 107-131.

Vermeire, K., Heremans, H., Vandeputte, M., Huang, S., Billiau, A., and Matthys, P. (1997). Accelerated collagen-induced arthritis in IFN-gamma receptor-deficient mice. J. Immunol. 158, 5507-5513.

Wang, Z., Hong, J., Sun, W., Xu, G., Li, N., Chen, X., Liu, A., Xu, L., Sun, B., and Zhang, J.Z. (2006). Role of IFN-gamma in induction of Foxp3 and conversion of CD4+ CD25− T cells to CD4+ Tregs. J. Clin. Invest. 116, 2434-2441.

Weiss, W.R., Sedegah, M., Beaudoin, R.L., Miller, L.H., and Good, M.F. (1988). CD8+ T cells (cytotoxic/suppressors) are required for protection in mice immunized with malaria sporozoites. Proc. Natl. Acad. Sci. 85, 573-576.

Willenborg, D.O., Fordham, S., Bernard, C.C., Cowden, W.B., and Ramshaw, I.A. (1996). IFN-gamma plays a critical down-regulatory role in the induction and effector phase of myelin oligodendrocyte glycoprotein-induced autoimmune encephalomyelitis. J. Immunol. 157, 3223-3227.

Wilson, M.T., Johansson, C., Olivares-Villagómez, D., Singh, A.K., Stanic, A.K., Wang, C.-R., Joyce, S., Wick, M.J., and Kaer, L.V. (2003). The response of natural killer T cells to glycolipid antigens is characterized by surface receptor down-modulation and expansion. Proc. Natl. Acad. Sci. 100, 10913-10918.

Wu, D., Xing, G.-W., Poles, M.A., Horowitz, A., Kinjo, Y., Sullivan, B., Bodmer-Narkevitch, V., Plettenburg, O., Kronenberg, M., Tsuji, M., et al. (2005). Bacterial glycolipids and analogs as antigens for CD1d-restricted NKT cells. Proc. Natl. Acad. Sci. U. S. A. 102, 1351-1356.

Wu, D., Zajonc, D.M., Fujio, M., Sullivan, B.A., Kinjo, Y., Kronenberg, M., Wilson, I.A., and Wong, C.-H. (2006). Design of natural killer T cell activators: Structure and function of a microbial glycosphingolipid bound to mouse CD1d. Proc. Natl. Acad. Sci. U. S. A. 103, 3972-3977.

Xing, G.-W., Wu, D., Poles, M.A., Horowitz, A., Tsuji, M., Ho, D.D., and Wong, C.-H. (2005). Synthesis and human NKT cell stimulating properties of 3-O-sulfo-α/β-galactosylceramides. Bioorg. Med. Chem. 13, 2907-2916.

Yang, G., Schmieg, J., Tsuji, M., and Franck, R.W. (2004). The C-Glycoside Analogue of the Immunostimulant aα-Galactosylceramide (KRN7000): Synthesis and Striking Enhancement of Activity. Angew. Chem. Int. Ed. 43, 3818-3822.

Yang, J.-Q., Singh, A.K., Wilson, M.T., Satoh, M., Stanic, A.K., Park, J.-J., Hong, S., Gadola, S.D., Mizutani, A., Kakumanu, S.R., et al. (2003). Immunoregulatory Role of CD1d in the Hydrocarbon Oil-Induced Model of Lupus Nephritis. J. Immunol. 171, 2142-2153.

Spiegel, S., et al., "Role of Sphingolipid Metabolites in the Actions of Growth Factors and Cytokines," Growth factors and Cytokines in Health and Disease, vol. 1B, pp. 537-563, 1996, JAI Press, Greenwich, CT, US.

Uyl-De Groot, C.A., et al., "Immunotherapy with autologous tumor cell-BCG vaccine in patients with colon cancer: a prospective study of medical and economic benefits," Vaccine 2005;23:2379-2387.

Aharoni et al., "Therapeutic Effect of the Immunomodulator Glatiramer Acetate on Trinitrobenzene Sulfonic Acid-induced Experimental Colitis," Inflamm. Bowel Disease 2005;11(2):106-115.

Andersen, P., et al., "T-Cell Proliferative Response to Antigens Secreted by *Mycobacterium tuberculosis*," Infection and Immunity 1991;59(4):1558-1563.

Bamias, G., et al, "Proinflammatory Effects of $T_H2$ Cytokines in a Murine Model of Chronic Small Intestinal Inflammation," Gastroenterology 2005;128(3):654-666.

Carpenter, Z. K., et al., "Mucosal delivery of microparticle encapsuled ESAT-6 induces robust cell-mediated responses in the lung milieu," Journal of Controlled Release 2005;104:67-77.

Clemens, J.J., et al., "Synthesis of benzimidazole based analogues of sphingosine-1-phosphate: discovery of potent subtype-selective $S1P_4$ receptor agonists," Bioorg. Med. Chem. Lett. 2004;14(19):4903-4906.

Davis, M.D., et al., "Sphingosine 1-phosphate analogs as receptor antagonists," J. Biol. Chem. 2005;280(11):9833-9841.

Desai, N. N., et al., "Sphingosine 1-phosphate, a metabolite of sphingosine, increases phosphatidic acid levels by phospholipase D activation," J. Biol. Chem. 1992;267:23122-23128.

Doherty, T. M., "New vaccines against tuberculosis," Tropical Medicine and International Health 2004;9(7):818-826.

Dubos, R., "The Effect of Sphingomyelin on the Growth of Tubercle Bacilli," Journal of Experimental Medicine 1948;88:73-79.

Dumont, F. J., "Fingolimod. Mitsubishi Pharma/Novartis," IDrugs 2005;8(3):236-253. (Abstract only).

Freidag, B. L., et al., "CpG Oligodeoxynucleotides and Interleukin-12 Improve the Efficacy of *Mycobacterium bovis* BCG Vaccination in Mice Challenged with *M. tuberlulosis*," Infect. Immun. 2000;68:2948-2953.

Furrie, E., et al., "Induction of local innate immune responses and modulation of antigen uptake as mechanisms underlying the mucosal adjuvant properties of immune stimulating complexes (ISCOMS)," Vaccine 2002;20(17-18):2254-2262.

(56) References Cited

OTHER PUBLICATIONS

Gajewska, B. U., et al., "B7RP-1 Is Not Required for the Generation of Th2 Responses in a Model of Allergic Airway Inflammation but is Essential for the Induction of Inhalation Tolerance," J. Immunol. 2005;174(5):3000-3005.

Garg, S. K., et al., "Sphingosine 1-Phosphate Induces Antimicrobial Activity Both In Vitro and In Vivo," J. Infec. Dis. 2004;189:2129-2138.

Garg, S. K., et al., "Does sphingosine 1-phosphate play a protective role in the course of pulmonary tuberculosis?" Clin. Immunol. 2006;121:260-264.

Gorvel, J.P., et al., "*Brucella* intracellular life: from invasion to intracellular replication," Vet. Microbiol. 2002;90(104):281-297.

Hale, J. J., et al., "A rational utilization of high-throughput screening affords selective, orally bioavailable 1-benzyl-3-carboxyazetidine sphingosine-1-phosphate-1 receptor agonists," J. Med. Chem. 2004;47(27):6662-6665.

Hla, T., "Signaling and biological actions of sphingosine 1-phosphate," Pharm. Res. 2003;47:401-407.

Holten-Anderson, I., et al., "Combination of the Cationic Surfactant Dimethyl Dioctadecyl Ammonium Bromide and Synthetic *Mycobacterial* Cord Factor as an Efficient Adjuvant for Tuberculosis Subunit Vaccines," Infec. Immun. 2004;72(3):1608-1617.

Hovav, A.-H., et al., "Gamma Interferon and Monophospholyl Lipid A-Trehalose Dicorynomycolate Are Efficient Adjuvants for *Mycobacterium tuberculosis* Multivalent Acellular Vaccine," Infec. Immun. 2005;73(1):250-257.

Hsieh, M.-J., et al., "Incorporation of CpG oligodeoxunucleotide fails to enhance the protective efficacy of a subunit vaccine against *Mycobacterium tuberculosis*," Vaccine 2004;22:655-659.

Jin, Y., et al., "Sphingosine 1-phosphate is a novel inhibitor of T-cell proliferation," Blood 2003;101:4909-4915.

Johansen, K. A., et al., "Biochemical and Molecular Analysis of Phospholipase C and Phospholipase D Activity in *Mycobacteria*," Infec. Immun. 1996;64(8):3259-3266.

Kaiserlian, D., et al., "The mucosal immune system: from control of inflammation to protection against infections," J. Leukoc. Biol. 2005;78:311-318.

Kim, J. W., et al., "Synthesis and evaluation of sphingoid analogs as inhibitors of sphingosine kinases," Bioorg. Med. Chem. 2005;13(10):3475-3485.

Kusner, J. D., et al., "Activation of phospholipase D is tightly coupled to the phagocytosis of *Mycobacterium tuberculosis* or opsonized zymosan by human macrophages," J. Exp. Med. 1996;184:585-595.

Kusner, J.D., et al., "ATP-induced killing of virulent *Mycobacterium tuberculosis* within human macrophages requires phospholipase D," J. Immunol. 2000;164:379-388.

Kusner, J.D., et al., "ATP Stimulates Human Macrophages to Kill Intracellular Virulent *Mycobacterium tuberculosis* via Calcium-Dependent Phagosome-Lysosome Fusion," J. Immunol. 2001;167(6):3308-3315.

Leirião, P., et al., "Survival of protozoan intracellular parasites in host cells," EMBO Reports 2004;5(12):1142-1147.

Lim, H.S., et al., "Syntheses of sphingosine 1-phosphate analogues and their interaction with EDG/S1P receptors," Bioorg. Med. Chem. Lett. 2004;14(10):2499-2503.

Liscovitch, M., et al., "Phospholipase D; Molecular and cell biology of a novel gene family," Biochem. J. 2000;345:401-415.

Meier, R., et al., Chemical Abstracts 54:93107, 1960.

Mielke, M. E. A., et al., "Cytokines in the induction and expression of T-cell-mediated granuloma formation and protection in the murine model of listeriosis," Immunol. Rev. 1997;158:79-93.

Moller, D. R., et al., "What causes sarcoidosis?" Curr. Op. Pulmon. Med. 2002;8:429-434.

Monteleone, I., et al., "Immunoregulation in the gut: success and failures in human disease," Gut 2002;50(Supp. III):iii60-iii64.

Murakami, T., et al., "Synthesis and biological properties of novel sphingosine derivatives," Bioorg. Med. Chem. Lett. 2005;15(4):1115-1119.

Murata, N., et al., "Quantitative Measurement of Sphingosine 1-Phosphate by Radioreceptor-Binding Assay," Analytical Biochem. 2000;282:115-120.

Orlati, S., et al., "Sphingosine-1-Phosphate Activates Phospholipase D in Human Airway Epithelial Cells via a G Protein-Coupled Receptor," Arch. Biochem. Biophys. 2000;375(1):69-77.

Pfeifer, S., et al., "Beryllium-Induced Disturbances of the Murine Immune System Reflect Some Phenomena Observed in Sarcoidosis," Int. Arch. Allergy Immunol. 1994;104(4):332-339.

Pizarro-Cerda, J., et al., "Subversion of phosphoinositide metabolism by intracellular bacterial pathogens," Nature Cell Biol. 2004;6(11):1026-1033.

Raja, A., "Immunology of tuberculosis," Indian J. Med. Res. 2004;120:213-232.

Rook, G. A. W., et al., "Do successful tuberculosis vaccines need to be immunoregulatory rather than merely Th1-boosting?" Vaccine 2005;23:2115-2120.

Ruan, F., et al., "Chemical Synthesis of D-Erythro-Sphingosine-1-Phosphate, and Its Inhibitory Effect on Cell Motility," Bioorg. Med. Chem. Lett. 1992;2(9):973-978.

Santucci, M. B., et al., "Expansion of CCR5+ CD4+T-lymphocytes in the course of active pulmonary tuberculosis," Eur. Respir. J. 2004;24:638-643.

Santucci, M. B., et al., "Sphingosine 1-phosphate promotes antigen processing and presentation to CD4+ T cells in *Mycobacterium tuberculosis*-infected monocytes," Biochem. Biophys. Res. Comm. 2007;361:687-693.

Sartor, R. B., et al., "Targeting enteric bacteria in treatment of inflammatory bowel diseases: why how, and when," Curr. Opin. Gastroenterol. 2003;19(4):358-365.

Sciorra, V. A., et al., "Potent direct inhibition of mammalian phospholipase D isoenzymes by calphostin c.," Biochem. 2001;40:2640-2646.

Semenzato, G., et al., "Applied clinical immunology in sarcoidosis," Curr. Opin. Pulmon. Med. 2002;8:441-444.

Wierecky et al., "Dendritic cell-based cancer immunotherapy targeting MUC-1," Cancer Immunol. Immunother. 2005;55:63-67.

Yoshimoto, T., et al., "Positive Modulation of IL-12 Signaling by Sphingosine Kinase 2 Associating with the IL-12 Receptor β1 Cytoplasmic Region," J. Immunol. 2003;170 (3):1352-1359.

Journal of Biological Chemistry (2002), vol. 277, pp. 21453-21457, "The Immune Modulator FTY720 Targets Sphingosine 1-Phosphate Receptors", Brinkmann et al.

Journal of Infectious Diseases (2004), vol. 189, Jun. 1, 2004, pp. 2129-2138, "Sphingosine 1 Phosphate Induces Antimicrobial Activity Both in Vitro and In Vivo" Garg et al.

Current Topics in Medicinal Chemistry (2004), vol. 4, pp. 561-567, "NKT Cell-stimulating Synthetic Glycolopids as Potential Therapeutics for Autoimmune Disease", Yamamura et al.

Journal of Clinical Investigation (2004), vol. 114, pp. 1531-1537, Regulation of Immunity by Lysosphingolipids and their G-protein-coupled receptors, Goetzl and Rosen.

Rook et al., Annals of Rheumatic Diseases, 1993, 52: S30-S38.

\* cited by examiner

PROPHYLACTIC AND IMMUNOMODULATORY COMPOSITIONS AND USES

The present invention relates to uses of sphingosine derivative compounds, such as D-erythro-sphingosine 1-phosphate (S1P) and related compounds (whether naturally occurring or synthetic) as adjuvants to vaccines and/or immunomodulators in the context of prophylaxis and prevention of disease, including vaccination with live, dead, genetic or subunit vaccines, particularly against tuberculosis, and also for the treatment and prevention of autoimmune diseases, particularly autoimmune diseases triggered or worsened by infection and/or by contact with microorganisms, such as Crohn's disease and sarcoidosis. Such compounds are characterized in that they stimulate macrophagic phospholipase D (PLD), promote phagolysosomal fusion and alter migration and cytokine secretion of immune cells to promote a concerted immune response that improves the outcome of the host upon infectious challenge, leading to a reduction of the infectious burden and amelioration of associated autoimmune complications.

Most particularly, the invention relates to compounds, compositions and methods for the prevention of infection and disease arising from *Mycobacteria*, especially *Mycobacterium tuberculosis* (Mtb), for instance by improved antigen presentation of vaccines, such as live mycobacterial vaccines that usually inhibit phagolysosomal fusion.

Immuno-defence mechanisms against infective agents include innate and acquired immunity responses developing during the early phases of the infection and later, respectively. The innate immune system (IIS) is non-specific and mediated by the activity of mononuclear, polymorphonuclear phagocytes and Natural Killer cells, whereas the acquired immune system (AIS) is specific and mediated by T and B lymphocytes, which are clonally distributed and characterised by specificity and memory. Physiologically, the IIS and AIS interact to affect an optimal immune response.

Antigen-presenting cells, such as macrophages and dendritic cells, are fundamental cellular components of IIS. These are able to phagocyte and digest exogenous particles by hydrolytic activity of lysosomal enzymes and exert an immunoregulatory effect on the MS by means of antigen-presentation and by secretion of cytokine and chemokines, leading to a concerted immune response.

During phagocytosis, firstly exogenous material adheres to the plasmatic membrane of macrophage and then the latter is enveloped within the cytoplasm resulting in a vesicle named a phagosome. This reaches the middle of the cell where it is fused with lysosomes, vacuolar organelles rich in hydrolytic enzymes active at acid pH, 4.5-5.0, thus generating a phagolysosome, a process that is mediated by phospholipase D (PLD) activation. PLD is a membrane enzyme widely diffused within the mammalian cells whose activity is under the control of hormones, neurotransmitters, growth factors and cytokines. During the maturation process of the phagolysosome, mediated through PLD, there is a progressive acidification of the phagosome whose pH decreases from neutral to acid values, namely 5 or less within the phagolysosome, activating metabolic mechanisms whose final goal is to make the macrophage able to eliminate the foreign microorganisms (viruses, bacteria, fungi, protozoa, parasites, etc.).

Some intracellular microorganisms, such as *Mycobacterium tuberculosis*, the etiological agent of tuberculosis (TB), are able, through various evasion mechanisms, to escape macrophage microbicidal mechanisms, including by inhibition of phagolysosomal fusion. The current most-widely used vaccine against TB, the *bacillus* Calmette-Guerin (BCG), which consists of a live, attenuated strain of *Mycobacterium bovis*, also inhibits phagolysosomal fusion in macrophages. The inhibition of phagolysosomal fusion by BCG contributes to its poor antigen-presentation and limits BCG's effectiveness as a vaccine and adjuvant.

Tuberculosis currently represents one of three most diffused diseases in the world together with acquired immunodeficiency syndrome (AIDS) and malaria.

Lack of effective prophylactic measures against TB (e.g. vaccines) is an important factor contributing to the increase of MTB occurrence.

Reports suggest that a successful outcome for the host upon Mtb infection depends largely upon appropriate cellular immunity (i.e. mediated by T cells). There are two broad (possibly overlapping) types of T-cells: Th1 (which secrete IL-2, IFN-gamma and appear to play a protective role in intracellular infections) and Th2 (which secrete Il-4, IL-5 and IL-10). The strength of a Th1 immune response is reported to relate directly to the clinical manifestations of the disease, whereas the strength of a Th2 immune response may exert a negative influence and prevent control of infection. In addition, a humoral immune response (i.e. mediated by B cells or antibodies) may also contribute to the response against TB. An appropriate concerted immune response is necessary to clear the infection effectively as well as crucial to prevent possible negative consequences of the immune response upon infection, such as excessive or chronic inflammation and tissue necrosis, perhaps associated with autoimmunity.

Infections are sometimes found associated to an inappropriate immune response that leads to lasting or chronic inflammation, often with a failure to clear effectively the associated infection, and to autoimmunity. Crohn's disease and sarcoidosis are two examples of autoimmune disease that have been reported as associated with infection, in particular with mycobacterial-like infection, and in which macrophages are recognized as playing an important role. The infection associated with excessive or chronic inflammation may be due to known pathogens, such as mycobacteria, or to other microbes not normally thought to be pathogenic, such as bacteria normally present in the gut.

Sphingolipids, including sphingosine and derivative compounds, like D-erythro-sphingosine 1-phosphate (S1P), are bioactive lipids with immunoregulatory activity. For example, S1P, a naturally-occurring, polar sphingolipid, was shown to increase PLD activity in macrophages, promote phagolysosomal fusion in Mtb-infected macrophages and, given at concentration close to physiologic ones, was reported to induce antimicrobial activity in human macrophages leading to the intracellular killing of TB. When S1P was intravenously injected in MTB-infected mice, S1P significantly reduced mycobacterial growth and pulmonary tissue damage. S1P has thus been suggested as a promising new antimycobacterial drug for treatment of human tuberculosis (Fraziano et al., International Publication Number: WO 03/045365. "IMMUNOREGULATOR COMPOUNDS").

Sphingolipids, including S1P, also have direct effects on immune cells other than macrophages: when administered to dendritic cells in vitro, S1P has been reported to alter the secretion of cytokine profiles to alter Th1/Th2 responses. In addition, it is recognized that S1P influences cell migration, including migration of dendritic cells and lymphocytes, as well as cell proliferation. S1P has also been reported to inhibit activation and proliferation of T cells (Jin et al., Blood 2003 Vol. 101:4909-4915). In conclusion, sphingolipids, including derivatives of sphingosine such as S1P, are capable of exerting directly a number of various effects on various immune cells.

However, there is still a requirement to provide more effective prophylactics against infectious diseases such as TB, and to provide immunomodulators that aid in preventing and treating such diseases, as well as autoimmune diseases.

It is thus an aim of the present invention to solve the above problems that are presented in the art, and to provide such prophylactics, and immunomodulators. It is also an aim of the present invention to provide vaccines, pharmaceutical compositions and uses which aid in the prevention, and in some cases treatment of certain diseases.

The present invention results from the observation that S1P increases antigen presentation in the context of vaccines (especially in live vaccines by virtue of immunomodulation and by induction of phagolysosomal fusion); that S1P is able to exert positive and lasting immunoregulatory effects when used as an adjuvant and—preferably in the presence of vaccination (either with a live, dead, genetic or subunit vaccine), but also in some cases in the absence of a vaccine—S1P is able to modulate the immune response to promote a long-lasting concerted immune response that prevents effective infection or re-infection of Mtb, improve the outcome of the host in the event of an infectious challenge, leading to a reduction of the infectious burden and amelioration of associated autoimmune complications.

Whereas it has been suggested that certain sphingosine compounds may be useful in treating particular infectious diseases, either as directly antimicrobial (in the absence of host cells, such as described in U.S. Pat. No. 6,147,118) or through their immunomodulatory activity (e.g. Fraziano et al., International Publication Number: WO 03/045365 "IMMUNOREGULATOR COMPOUNDS"), an original and unexpected aspect of the present invention is that sphingosine compounds can be used in vaccines, for instance in the prevention or prophylactic treatment of infectious diseases. When used as an adjuvant to vaccines, sphingosine compounds may lead to effective or improved immunity and long-lasting immune regulation.

Furthermore, although certain sphingosine compounds have been suggested as potential therapeutics for autoimmune disease (e.g. Yamamura et al, Current Topics in Medicinal Chemistry, 2004, 4:561-567) and have been postulated to be applicable for the treatment of autoimmune disease through their regulatory activity of S1P receptors, particularly in lymphocytes and cells of the acquired immune system, (e.g. Brinkmann et A, 2002, JBC, 277(24): 21453-21457 or Goetzl & Rosen, 2004, 114(11):1531-1537; Baumruker et al., International Publication Number: WO 03/097028; Foster, International Publication Number: WO 04/028521 and Buehlmayer et al, International Publication Number: WO 04/024673), a novel and unexpected aspect of the present invention is that sphingosine compounds, in particular sphingosine compounds that increase the antimicrobial activity of cells of the native immune system (e.g. macrophages and dendritic cells), and which may allow long-term immunity in the context of vaccines, can also be used for the treatment of autoimmune diseases, particularly when the autoimmune disease is associated with infection.

Thus, it is a further aim of the present invention to provide new means for the prevention of infections, whether derived from known pathogens like *Mycobacterium tuberculosis* or derived from other microbes not normally considered pathogenic, such as gut bacteria, as well as for the prevention and treatment of autoimmune complications associated with these infections, particularly chronic inflammations such as Crohn's disease or sarcoidosis.

Further, the present invention has the object of regulating the immune response to increase the effectiveness of vaccines (including live, dead, genetic and subunit vaccines).

Therefore, the present invention aims to provide compounds to be used as immunomodulators able to induce, restore or increase the efficiency of immuno-defence mechanisms, whether on their own or in combination (e.g. with vaccines), for prophylaxis against infections, principally (but not exclusively) infections resulting from bacteria and specifically *Mycobacterium tuberculosis*, and also for the prevention and treatment of associated autoimmunity (e.g. Crohn's disease and sarcoidosis).

Such compounds, which are sphingosine derivatives or analogs, like D-erythro-sphingosine 1-phosphate (S1P), are able to stimulate in a dose-dependent effect the macrophage PLD both in presence and absence of infection. In addition, such compounds promote phagolysosomal fusion (thus promoting antigen presentation even of live mycobacterial vaccines, which usually inhibits phagolysosomal fusion) and alter migration and cytokine secretion of immune cells to promote a concerted immune response that improves the outcome of the host upon infectious challenge or in susceptibility to autoimmune disease associated to infection.

An object of the invention is to provide pharmaceutical compositions containing sphingosine derivatives, particularly S1P, and methods for their preparation. These compositions are preferably in the form of solutions, emulsions or suspensions, but can also be microencapsulated or administered (for example, by injection into the bloodstream or by feeding) from cells or organisms (or derivatives thereof) containing S1P (whether live or dead, and whether naturally-occurring or recombinant). These compositions can also be used in combination with other compounds, such as vaccines, either simultaneously with vaccines or at different times.

The invention further provides use of a sphingosine compound, or a derivative of a sphingosine compound, in the manufacture of an immunomodulation medicament effective in the treatment and/or prevention of an autoimmune disease associated with infection.

Thus the present invention makes use of sphingosine compounds and derivatives of such compounds. In the context of the present invention, the term derivatives is intended to include compounds that are structurally related to sphingosine compounds having a similar or the same effect as sphingosine compounds, most particularly sphingosine-1-phosphate, as well as analogues of any such sphingosine compounds or structurally related compounds.

Sphingosine compounds, derivatives and analogues included in the present invention can readily be identified by known assays, such as the assay for therapeutically efficient candidate compounds disclosed in WO 03/045365, the content of which is incorporated herein by reference. This assay can be used to assess the capability of candidate compounds, derivatives or analogues to promote stimulate, increase or accelerate the maturation of phagolysosomes in infected macrophages. The assay comprises the following in vitro procedure:

(a) bringing the macrophages into contact with fluorescein-labelled and phagocytosis-susceptible particles, and successively treating with candidate molecule, compound, derivative, or analogue;

(b) monitoring the fluorescence emission and the maturation of phagolysosomes detected by the decrease of fluorescence emission; and (c) comparing the decrease in fluorescence emission to the decrease in fluorescence emission detected in the same procedure in the absence of the candidate molecule.

The particles used in the assay may be microorganisms, or synthetic particles and may be labelled with fluorescein isothiocyanate. Preferably the macrophages are brought into contact with bacteria at the multiplicity of infection (MOI) from 0.1:1 and incubated from 1 hour to 7 days at 37° C. After incubation, the macrophages are treated with the substance to be tested, whose activity is evaluated for a period of from 15 to 90 minutes, preferably about 30 minutes. The fluorescence may be monitored, for example, by means of a fluorometer, a flow cytometer, or a fluorescence microscope, detecting the biogenesis of mature phagolysosomes through the emission decrease of fluorescence signal. Decrease in the fluorescence emission is compared with that observed according to the same procedure in the absence of candidate molecule. Any substance able to promote, stimulate, increase or accelerate the maturation of phagolysosomes in macrophages will be detected by being able to modify the emission profile of the fluorimetric signal when compared with the observed model in the absence of the substance.

Specific examples of derivatives and analogues that may be used in the present invention include: include N,N-dimethylsphingosine, DL-threo-dihydrosphingosine, 1-benzyl-3-carboxyazetidine and N-acetylsphingosine ($C_2$-ceramide), as well as phosphate and phosphonate analogs, such as 3-(N-benzyl or alkyl or alkylamino) aminopropylphosphonic acid. Further such compounds are disclosed in the following published documents, the contents of which are incorporated herein by reference:

J. Med. Chem. 2004 Dec. 30; 47(27):6662-5, "A rational utilization of high-throughput screening affords selective, orally bioavailable 1-benzyl-3-carboxyazetidine sphingosine-1-phosphate-1 receptor agonists.", Hale J J, Lynch C L, Neway W, Mills S G, Hajdu R, Keohane C A, Rosenbach M J, Milligan J A, Shei G J, Parent S A, Chrebet G, Bergstrom J, Card D, Ferrer M, Hodder P, Strulovici B, Rosen H, Mandala S;

Bioorg. Med. Chem. 2005 May 16; 13(10):3475-85, "Synthesis and evaluation of sphingoid analogs as inhibitors of sphingosine kinases.", Kim J W, Kim Y W, Inagaki Y, Hwang Y A, Mitsutake S, Ryu Y W, Lee W K, Ha H J, Park C S, Igarashi Y;

Bioorg. Med. Chem. Lett. 2005 Feb. 15; 15(4):1115-9, "Synthesis and biological properties of novel sphingosine derivatives.", Murakami T, Furusawa K, Tamai T, Yoshikai K, Nishikawa M;

J. Biol. Chem. 2005 Mar. 18; 280(11):9833-41., E pub 2004 Dec. 8., "Sphingosine 1-phosphate analogs as receptor antagonists.", Davis M D, Clemens J J, Macdonald T L, Lynch K R;

Bioorg. Med. Chem. Lett. 2004 Oct. 4; 14(19):4903-6., "Synthesis of benzimidazole based analogues of sphingosine-1-phosphate: discovery of potent, subtype-selective S1P4 receptor agonists.", Clemens J J, Davis M D, Lynch K R, Macdonald T L; and Bioorg. Med. Chem. Lett. 2004 May 17; 14(10):2499-503, "Syntheses of sphingosine-1-phosphate analogues and their interaction with EDG/S1P receptors.", Lim H S, Park J J, Ko K, Lee M H, Chung S K.

Typically the autoimmune disease is a disease that is associated with infection. The infection may be any infection, but is typically an infection leading to chronic inflammation, and may be caused by a known pathogen, such a mycobacterial pathogen, or by a microbe not normally thought to be pathogenic, such as common gut bacteria. The autoimmune disease may be any autoimmune disease, but preferably is selected from Crohn's disease and sarcoidosis.

The invention also provides use of a sphingosine compound, or a derivative of a sphingosine compound, in the manufacture of a vaccine, effective in the treatment and/or prevention of an infectious disease, and further, use of a sphingosine compound, or a derivative of a sphingosine compound, in the manufacture of an immunomodulation medicament, effective in the prevention of an infectious disease.

Although the infectious disease is not especially limited, it is preferred that the infectious disease is caused by one or more viruses, bacteria, fungi, protozoa or parasites. It is especially preferred that the infectious disease is caused by an intracellular pathogen. Typical intracellular pathogens include *Mycobacterium tuberculosis, Bacillus anthracis* and *Listeria monocytogenes*.

Further provided by the invention is use of a sphingosine compound, or a derivative of a sphingosine compound, in the manufacture of a vaccine effective in the treatment and/or prevention of cancer. In some embodiments the vaccine may comprise a component derived from an infective agent, for example the vaccine may be a BCG or dendritic vaccine. The cancer may be any cancer, but it is preferred that the cancer is colon cancer.

In all of the above uses of the invention, a preferred embodiment is one in which the sphingosine compound is used as an adjuvant.

The invention also provides a vaccine effective in the treatment and/or prevention of an autoimmune disease, comprising a sphingosine compound, or a derivative of a sphingosine compound. The autoimmune disease is typically one as already described above.

A vaccine is also provided by the invention, which is effective in the treatment and/or prevention of an infectious disease, comprising a sphingosine compound, or a derivative of a sphingosine compound. It is generally preferred that the infectious disease is one as described above. Typically the antigen present is BCG or *Mycobacterium tuberculosis*, whether live dead or a derivative thereof, and macrophages are treated with D-erythro sphingosine 1-phosphate.

Further provided by the invention is a pharmaceutical composition comprising a prophylactically-effective amount of a sphingosine compound, or a derivative of a sphingosine compound, alone or together with one or more pharmaceutically acceptable antigens, adjuvants and/or excipients. The composition may be in any suitable form, depending on patient and disease state, but typically the composition is in the form of solid or solution, emulsion or suspension. In some embodiments it may be in the form of microencapsulated particles, an aerosol, or a liposomal suspension.

Typically, the compound is suitable for administration from cells or organisms or derivatives thereof. These cells or organisms may be live or dead, and may be naturally-occurring or recombinant. The cells or organisms contain the immunoregulatory compounds, and are administered either directly into the host, or indirectly by prior in vitro or ex vivo treatment of cells or tissues.

The composition may be administered in any desired manner, but in preferred embodiments it is administered by injection or oral administration.

The composition may contain the sphingosine compound or derivative in any desirable concentration, depending on patient and disease state, but in some preferred embodiments it contains the sphingosine compound in concentration of from 0.1 µM to 10 mM, more preferably from 0.1 µM to 10 µM.

The composition according to the invention may contain the sphingosine compound as the sole prophylactic or preventative or therapeutically effective agent or in association with other prophylactic or preventative active agents. Preferably, the other prophylactic or preventative active agents include vaccines, whether live, genetic, dead or subunit.

Typically, a prophylactically or preventatively-effective amount of the sphingosine compound is mixed with additional pharmaceutically acceptable substances. The additional pharmaceutically acceptable substances are not limited. In some embodiments they may be selected from surfactants, buffers, stabilisers, preservatives, anti-oxidants, adjuvants, or antigens, including vaccines, whether live, dead or subunit.

The sphingosine compound is not especially limited, provided that its prophylactic and/or therapeutic function is not impaired. Typically it is selected from D-erythro or L-threo sphingosine isomers, mono-, di- or tri-phosphates of sphingosine, and natural or synthetic analogs and derivatives of sphingosine capable of mimic their immunoregulating activity. The immunoregulating activity is not especially limited, and, for example, may be associated with the induction of phagolysosome maturation in macrophages or epithelial cells upon encountering an antigen. Alternatively, it may be associated with the activity increase of macrophage phospholipase D upon encountering an antigen, with the activity increase in cytokine secretion, the production increase of oxygen and/or nitrogen reactive intermediates in antigen-presenting cells, or the expansion of specific T cells against the antigens presented by antigen-presenting cells. In this case the antigen may be selected from a microbe or vaccine. The antigen presenting cells may be selected from dendritic cells, macrophages and monocytes.

Generally, the sphingosine compound is a compound having the following structure, or a salt or other derivative of this compound:

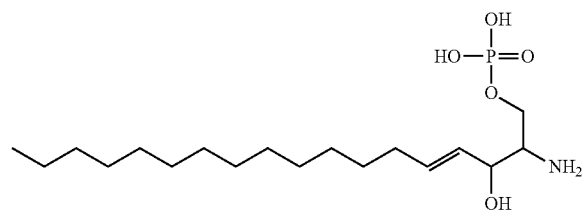 [SMILES: CCCCCCCCCCCCC/C=C/C(O)C(N)COP(=O)(O)O]

The most preferred sphingosine compound is D-erythro-sphingosine 1-phosphate (S1P), or a salt or other derivative of S1P.

The invention also provides a prophylactic method against an autoimmune disease or an infectious disease, which method comprises vaccinating a subject with a vaccine as defined above, or administering a pharmaceutical composition as defined above.

Further provided is a method to induce or restore or increase immunoregulatory activity which method comprises vaccinating a subject with a vaccine as defined above, or administering a pharmaceutical composition as defined above.

These methods may comprise administration of the vaccine or the pharmaceutical composition simultaneously, sequentially or separately to one or more antigens and/or excipients.

If further antigens and/or excipients are present, they may be selected from vaccines, whether live, dead, genetic or subunit, and allergens.

Typically the antigen present is BCG or *Mycobacterium tuberculosis*, whether live dead or a derivative thereof, and macrophages are treated with D-erythro sphingosine 1-phosphate.

S1P causes phagolysosomal fusion in BCG/mycobacterial infection (Garg et al., 2004, JID Vol. 189, pp. 2129 to 2137), leading to better antigen presentation, particularly useful in live vaccines. Because phagolysosomal fusion helps to eradicate infections, and because infection often contributes to inflammation in autoimmune disorders, S1P may be clinically useful in the treatment of autoimmune diseases, such as Crohn's disease (reported to be associated with *Mycobacterium avium* paratuberculosis infection) or sarcoidosis (reported to be associated with tuberculosis or a viral infection).

S1P is an immunoregulator and macrophage activator, which alters cytokine secretion of immune cells. This characteristic is particularly useful in dead or subunit vaccines, because an altered cytokine profile upon vaccination, for example minimizing local IL4 cytokine secretion (associated with a Th2 response), can increase the effectiveness of a TB-booster vaccine. Altering the local Th1/Th2 response may also reduce inflammation in the case of autoimmune disorders.

S1P reduces T-cell motility and prevents inflammatory responses at the site of infection. Stopping lymphocyte infiltration at a site of inflammation helps reduce necrosis in the lungs of a TB model (Garg et al., 2004, JID Vol. 189, pp. 2129 to 2137); further, S1P administered to mycobacterial-infected macrophages promotes phagolysosomal fusion (BCG vaccine also prevents fusion, which can be reversed with S1P); by association, the same characteristics may reduce inflammation and necrosis in autoimmune disorders, such as commonly found in the gut of Crohn's patients, particularly when bacteria infiltrating the gut tissues causes prolonged inflammation. Temporary prevention of T-cell infiltration also alters the outcome of vaccination: for example, in the case of TB vaccination this may lead to regulated antigen presentation and to increased immunity.

Immunomodulating compounds according to the present invention are sphingosine derivatives and analogs (whether naturally occurring or synthetic). Sphingosine is a long chain amino alcohol constituent of cellular membranes and together with sphingosine-1-phosphate is a member of a class of second lipid messengers produced in response to growth factors. Sphingosine itself and its derivatives can be both in erythro and threo conformation, (D) and (L) configuration and cis and trans across the double bond. Sphingosine derivatives and their analogs are also able to mimic immunomodulating activity, particularly those selected among D-erythro or L-threo and monophosphates, diphosphates, triphosphates thereof and more particularly D-erythro sphingosine 1-phosphate (S1P).

Administration of sphingosine derivatives, even before infectious challenge, induces an increase of microbicidal activity, particularly bactericidal and specifically mycobactericidal, upon subsequent infection of both animal and human macrophages and epithelial cells, which can be detected as a decrease of colony forming pathogen units. Such an immunomodulating activity is associated to the induction of phagolysosome maturation and increase of the activity of macrophage phospholipase D in pathogen infected cells and increase of the production of oxygen and/or nitrogen reactive intermediates. Although the ineffectiveness of Mtb in epithelial cells is not as high as in macrophages, epithelial cells are important in preventing Mtb from further infiltration and therefore, form a "line of defence" against spread of infection. S1P administered before infection increases the capacity of macrophages and epithelial cells to control an infection and therefore S1P may prove a useful prophylactic against further infection and prevent dissemination of pathogenic bacilli or of the normal gut flora in animals and humans, particularly in the gut.

Administration of S1P to TB-infected macrophages induces expansion of Mtb specific T cells, demonstrating the capacity of S1P to promote long-lasting anti-mycobacterial immunoregulation, which involves cell-mediated immunity, a finding that can be applied in the context of disease prevention and prophylaxis and, specifically for improving vaccine efficiency.

Administration of S1P in mice at levels in which immunoregulatory activity can be measured appears safe, suggesting that S1P may be administered safely directly in animals or humans to exert immunoregulatory prophylactic, therapeutic or vaccine-enhancing activity.

Therefore the above sphingosine derivative compounds to be used as immunomodulators and for related uses in the preparation of medicaments and vaccines with immunoregulating activity, e.g. associated to the above phenomena, are object of the present invention.

Sphingosine derivatives as immunoregulating compounds according to the present invention can be used advantageously in the prophylaxis and prevention of infections resulting from any pathogen as viruses, bacteria, fungi, protozoa and other parasites and particularly *Mycobacterium tuberculosis, Bacillus anthracia* or *Listeria monocytogenes.*

These compounds can also be used advantageously to prevent and treat autoimmune disease associated to infections and particularly Crohn's disease and sarcoidosis.

The present invention also provides pharmaceutical compositions comprising prophylactically or therapeutically active amounts of a sphingosine derivative compound together with one or more pharmaceutically acceptable antigen, adjuvant and/or excipient (including vaccines).

These compositions can contain the immunoregulating compound as the sole active agent when used in a treatment for simple promotion of native or acquired immunodefences or can contain the same in association with other prophylactic (such as vaccines), anticancerous or microbicidal medicaments or compositions.

Pharmaceutical compositions according to the present invention can be formulated according to known methods that include the presence of a pharmaceutically acceptable vehicle both in solid and liquid form. Examples of these vehicles and formulation methods are reported in specialised literature. Pharmaceutical compositions suitable for immunoregulating activity must contain an effective amount of the active principle according to the present invention. In the case of liquid compositions such an amount corresponds to 0.1 microM to 10 mM, preferably from 1 to 200 microM, which are concentrations present in the medium in cells grown in vitro at which effects can be observed, and the concentration of which 100 microliters is effective per mouse when administered intravenously. In the case of solid compositions the amount expressed as micrograms corresponding to the above concentrations can be used. Pharmaceutical compositions according to the present invention are administered to a subject (or to cells in vitro or ex-vivo) in such amount that is effective for successful prevention or treatment of the related disease. Relative amount can be varied depending on a multiplicity of factors like individual conditions, weight, sex and age, as well as method and site of administration (e.g. larger amounts may be administered in a targeted manner, for example directly into the gut by oral administration to prevent infection, since the concentration of administered compound may not rise systemically). Preferred formulations are liquid compositions in the form of solutions, suspensions or emulsions to be administered by oral, inhaled (e.g. via aerosol) or parenteral route; other formulations include microencapsulation and also administration (for example, by injection or feeding) from cells or organisms (or derivatives thereof, whether live or dead, and whether naturally-occurring or recombinant) containing the immunoregulatory compounds, either directly into the host, or indirectly by prior in vitro or ex vivo treatment of cells or tissues. These compositions can also be used in combination with other compounds, such as vaccines, either simultaneously with vaccines or at different times. Due to the chemical characteristics of sphingosine derivatives the inclusion thereof within liposomes or emulsions is particularly preferred. According to the present invention the immunoregulating compound can be administered typically in mixture with suitable pharmaceutical diluents, excipients or vehicles conveniently selected by taking in consideration the desired administration route.

Because the inventive compounds are soluble in hydroalcoholic solvents (water/ethanol), such solutions thereof are used as such, if suitable, or are used as starting reagent for the preparation of different pharmaceutical formulations. Further, the composition can contain pharmaceutically acceptable optional additives as surfactants, buffers, stabilisers, preservatives and antioxidants.

The preparation of the pharmaceutical compositions according to the invention includes methods known in the specific field. The immunomodulating compounds are mixed in solid or liquid form with suitable excipients, possibly with any desired optional additive, preferably in hydroalcoholic solutions, at concentrations from 0.1 microM to 10 mM, preferably from 0.5 microM to 1 mM or, in the case of solid compositions, at corresponding weight amounts. These solutions are then formulated in liquid compositions suitable to be administered, as solutions, suspensions, emulsions, or liposome-encapsulated (or other encapsulation method, such as in calcium alginate) or dried as powders or granules suitable to be formulated in solid compositions. In the case of liquid compositions 0.1 microM to 10 mM, preferably from 1 to 200 microM, are concentrations present in the medium in cells grown in vitro at which effects can be observed and the concentration of which 100 microliters is effective per mouse when administered intravenously.

The present invention also provides an in vitro method to induce or restore or increase the immunoregulatory activity of immune cells, preferably phagocytes, such as human macrophages, dendritic cells and mast cells. Immune cells cultured as described in the experimental section and treated with relevant antigens, such as vaccines (whether live, dead, genetic or subunit), susceptible to phagocytosis, for example at a pathogen/macrophage infection ratio (MOI) from 1:1 to 10:1 for a period from 1 to 24 hours are treated with solutions containing sphingosine derivatives according to the invention at concentrations from 0.1 μM to 10 mM, preferably from 1-200 μM, particularly from 1-10 μM, such as about 5 μM over an incubation period from 1 minute to 24 hours, preferably from 15 to 90 minutes. Suitable antigens are viruses, bacteria, fungi, protozoa, parasites, particularly *Mycobacterium tuberculosis* and, in particular, vaccines such as BCG, cell extracts and subunit vaccines. Immune cells, such as macrophages, are preferably treated with D-erythro sphingosine 1-phosphate.

The invention will be further illustrated by way of example only, with reference to the following specific embodiments, which describe reagents, conditions and procedure suitable for the practice of the invention.

EXAMPLE 1 S1P+BCG TO PREVENT TB

BCG is the most widely used vaccine against tuberculosis, but it is ineffective in producing long-lasting effective immunity and it is particularly ineffective in preventing TB in adults (Doherty, Tropical Medicine and International Health, Vol. 9 No 7, pp. 818-826). The cause of this lack of effectiveness may be related to a failure of correct antigen presentation, because BCG, like virulent Mtb, prevents lysosomal fusion occurring in macrophages, which are important antigen-presenting cells. In addition, it is known in the art that immunoregulators may improve vaccination-mediated immunity, such as reported upon BCG vaccination in combination with oligodeoxynucleotides containing cytidine phosphate guanosine (CpG) motifs (Freidag et al, 2000, Infect. Immun., Vol 68, pp. 2948-53). It is relevant that activation of sphingosine kinase, the primary enzyme for S1P production in cells, is able to induce IFN-gamma production in Th1 cells (Yoshimoto et al, 2003, Journal of Immunology, pp. 1352-1359), because IFN-gamma production and a Th1-mediated response is known to be associated with effective antimycobacterial immunity (Raja, 2004, Indian J Med. Res., Vol. 120, pp. 213-232).

The present invention relates to sphingosine compounds such as S1P given as an adjuvant to vaccines, in particular to a live BCG vaccine, in which S1P increases antigenicity of the vaccine and, by its immunoregulatory activity, induces improved long-lasting vaccine-immunity.

In particular, increased prophylaxis against TB infection using a live vaccine in combination of S1P may be achieved in the following way: in mice, for example BALB/c mice, a total of 0.1 to 200 nanomoles of S1P, preferably 1 to 20 nanomoles per mouse, can be added and mixed with prophylactic amounts of BCG vaccine (amounts of BCG required in well known in the art), prior to inoculation with the mixture.

In general, the efficacy of sphingosine compounds of the present invention (such as sphingosine-1-phosphate) as an adjuvant for a *Bacillus* Calmette-Guerin (BCG) vaccine can be tested using the following protocols. In particular, the protocol aims to test that:

a) BCG immunogenicity is increased when the sphingosine compound (e.g. S1P) is given as an adjuvant in mice, as measured by immunological markers such as cytokine responses, cell proliferation and antibody production, including dose responses to S1P b) Protection against virulent tuberculosis is improved when using the sphingosine compound (e.g. S1P) as an adjuvant to BCG (compared to BCG alone), as measured upon challenge with virulent TB in mice, including measurements of mice survival rates, extent of *bacillus* survival in spleen and lungs and histology for amount of inflammation in tissues.

In the following, S1P is used as an example of a sphingosine compound to be tested.

Phase 1—Testing BCG Immunogenicity

The BCG vaccine and S1P are given to 5 or 6 week-old C57BL/6 mice, normally intravenously (or alternatively as subcutaneous or intradermal injection). Group mice according to the following variables:

Saline control (no vaccination)

Mixture of a normal dose of BCG+0, 1, 5, 20 nmoles of S1P (as adjuvant)—the hydrophobicity properties of S1P ensure binding to the surface of the live vaccine, even in the presence of small amounts of detergent usually added to the vaccine to achieve a suspension of cells.

At weeks 1, 3 and 8, carry out the following analyses:

Peripheral blood, spleen and lung lymphocyte cultures, for cytokine measurements by ELISA (for method details: Holten-Andersen et al., Infection and Immunity, 2004, Vol 72, No. 3, p. 1608-1617). Measure cytokines expressed upon PPD stimulation.

IFN-gamma

TNF-alpha

IL2, IL4, IL10, IL12

FACS analyses of lymphocytes from vaccinated and control mice, isolated from lungs. Culture cells in the presence of PPD for 72 hours before staining (+control wells without antigen). Measure CD4, CD8 cells and intracellular IFN-gamma (see: Holten-Andersen et al., Infection and Immunity, 2004, Vol 72, No. 3, p. 1608-1617).

Histological analysis of lungs

At week 8 (prior to TB infection), also measure BCG CFU in spleen and lungs

Phase 2—Testing BCG/S1P Protection

At week 8 post-vaccination, infect the remaining mice with *M. tuberculosis* (Erdman) cultured from infected organs (Andersen et al., Infect. Immun., 1991, Vol. 59, p 1558-1563). Use aerosol infection with inoculum of 30-40 CFU per mouse (see: Holten-Andersen et al., Infection and Immunity, 2004, Vol 72, No. 3, p. 1608-1617), or a higher dose of intravenous, subcutaneous or intradermal.

Survival rates of infected mice are measured, monitoring weight loss and difficulty of breathing.

A subset are sacrificed at week 6 after TB infection, for detailed analysis:

CFU counts: Mycobacterial cultures from lungs grown on 7H11 plates, containing 2-thiophenecarboxylic acid anhydride (to selectively inhibit BCG growth)

Histological analysis of lungs

When following the above protocols using an appropriate number of mice and experiments for appropriate statistical analysis, it can be demonstrated that S1P itself has novel, unexpected and advantageous properties as a vaccine adjuvant, as determined by some of the parameters measured.

Experimental methods similar to some of those described above for testing of the efficacy of an adjuvant may additionally be described in more detail the following references:

Garg et al., JID, 2004, Vol 189, p 2129-38

Holten-Andersen et al., Infection and Immunity, 2004, Vol 72, No. 3, p. 1608-1617

Hsieh et al, Vaccine, 2004, Vol 22, p 655-659

Andersen et al., Infect. Immun., 1991, Vol. 59, p 1558-1563

Hovav et al, Infection and Immunity, 2005, Vol 73, No. 1, p 250-257

BCG has also been used in the context of cancer treatment (Uyl-de Groot et al, 2005, Vaccine, 23, pp. 2379-2387). In the present invention, S1P is revealed to be effective as an immunomodulator of vaccines, such as BCG and dendritic vaccines, for the treatment of cancer, for example colon cancer.

EXAMPLE 2 S1P+ TO DEAD OR SUBUNIT VACCINES TO PREVENT TB

It is known that the immunogenicity and protective efficacy of subunit vaccines may be increased by lipid adjuvants, for example monophosphoryl lipid A-trehalose dicorynomycolate (Bibi), which improves vaccine immunity conferred by TB protein antigens (Hovav et al 2005, Infection and Immunity Vol. 73, No 1, pp. 250-557). Moreover, it has been reported that successful TB vaccines may need to be immunoregulatory rather than merely Th1 boosting (Rook et al, 2005, Vaccine, Vol. 23, pp. 2115-2120).

The present invention relates to S1P as a novel immunoregulatory adjuvant to dead or subunit vaccines. In particular, increased prophylaxis against TB infection using a subunit or dead vaccine in combination of S1P may be achieved in the following way: in mice, for example BALB/c mice, a total of 0.1 to 200 nanomoles of S1P, preferably 1 to 20 nanomoles per mouse, can be added and mixed with prophylactic amounts of dead or subunit vaccine prior to inoculation with the mixture. In the case of an anti-mycobacterial vaccine, antigens may be cell-culture filtrates of mycobacteria or recombinant antigens, such as ESAT-6, 85B or CFP21, all administered in prophylactically-effective amounts, which are known in the art (for example, 5 micrograms of each antigen per mouse). Alternative methods of vaccine and or S1P administration can also be used, as described in example 1 (above).

For instance, in alternative embodiments S1P can be given orally, for example as an additive in the diet or by gastric infusion, to increase the levels of S1P found in plasma, preferably to above 200 nM, most preferably above 600 nM. As a further alternative, S1P can be given by aerosol administration directly into the lungs, preferably to final concentrations equivalent to above 1 µM, as suggested by measurements of S1P in bronchoalveolar lavages of non-TB patients: aerosol administration increases mucosal immunity and methods are known in the art, for example by microencapsulation with calcium alginate beads or as described by Carpenter et al, (2005, Journal of Controlled Release, Vol. 104, pp. 67-77). In addition, S1P can be administered as a "classical" immunoregulatory adjuvant—i.e. together and simultaneously with the vaccine—or separately, but at a time proximal to the time of BCG vaccination, preferably within a period of 1 week before or after vaccination.

EXAMPLE 3 S1P TO TREAT OR PREVENT CROHN'S DISEASE

Crohn's disease is an autoimmune disease characterized by a chronic inflammatory process in the gut, in which CD4+ T-cells represent the vast majority of activated mononuclear cells infiltrating the gut. There is evidence in the literature that CD4+ T-cells play a key role in the pathogenesis of tissue damage in Crohn's disease (Monteleone et al, 2002, Gut, Vol. 50, Suppl. III, pp. 11160-64). There is also evidence that infections, particularly *Mycobacterium paratuberculosis* infections, either induce autoimmune disease or contribute to the pathology in Crohn's disease (Sartor et al, 2003, Curr. Opin. Gastroenterol., Vol. 19, No 4, pp. 358-365) and, therefore, eradication of infection may alleviate the disease. There is also clear evidence that the intestinal microbiota serves as a trigger for intestinal inflammation and that rapid and efficient killing by macrophages prevents further immune involvements, which may lead to disease (Kaiserlian et al., 2005, J Leukoc. Biol., May 13; Epub ahead of print). Moreover, there is ample evidence that cytokines participate in disease development in other mouse models of colitis, such as in SAMP1/YitFc mice (Bamias et. al, 2005, Gastroenterology, Vol. 128, No 3, pp 654-666). In addition, a mouse model of colitis (trinitrobenzene sulfonic acid—TNBS-induced colitis) can be treated with the immunomodulator compound glatiramer acetate (Aharoni et al, 2005, Inflamm. Bowel Disease, Vol. 11, No. 2, pp. 106-115), suggesting that other immunomodulators may also be useful for treatment.

S1P, when injected intravenously in mice, is known in the art to induce antimycobacterial activity in experimental tuberculosis infection, and therefore is already known as a potential therapeutic agent against infectious disease, particularly against TB. It is an object of the present invention that S1P is not just able to treat infectious disease, but also able to prevent microbial disease infecting an individual, and may be administered to induce effective prophylaxis. A gene involved in the production of S1P (sphingosine kinase 2) is, considering the effectiveness of S1P in preventing TB, a strong candidate (one of approximately 60 genes) for conferring genetic susceptibility to TB in mice, because it is located within a genetic susceptibility locus (Tlr-3). This finding suggests that levels of S1P prior to infection determine the outcome of TB infection and that abnormalities in sphingosine metabolism, particularly in S1P metabolism, are associated with increased susceptibility to infection and a weak long-term immunity against microbes such as Mtb, which may lead to chronic inflammation, as seen in tuberculosis and Crohn's disease.

The present invention relates to the use of S1P as an immunomodulator in the prevention and treatment of autoimmune diseases, such as inflammatory bowel diseases and, in specific, of Crohn's disease. In particular, prevention and/or treatment of inflammatory bowel disease (IBD) with S1P can be achieved in the following way: in an appropriate animal model of IBD, such as in TNBS-induced colitis mouse model or in SAMP1/YitFc mice, increasing gut levels of S1P will prevent and/or ameliorate the signs and symptoms of gut pathology. S1P in the gut may be increased by injecting intravenously, for example once a week, a total of 0.1 to 200 nanomoles of S1P, preferably 1 to 20 nanomoles per mouse. Alternatively, S1P can be administered directly into the gut, for example via oral administration or as an additive in the diet, or by gastric infusion, to increase the local levels of S1P in gut tissues. S1P induces macrophages to clear infections in the gut that participate in pathology and reduces inflammation by preventing T cells from infiltrating the gut.

EXAMPLE 4 S1P TO TREAT OR PREVENT SARCOIDOSIS

Sarcoidosis is an autoimmune disease most commonly affecting the lung, characterized by a marked TM activation (Semenzato et al, 2002, Current Opinion in Pulmonary Medicine, Vol. 8, pp. 441-444). Recent findings suggest that the etiology of systemic sarcoidosis is linked to genetically determined enhanced Th1 immune responses to a limited number of microbial pathogens, including specifically *M. tuberculosis* (Moller & Chen, 2002, Current Opinion in Pulmonary Medicine, Vol. 8, pp. 429-434).

In one aspect the present invention relates to the use of sphingosine compounds such as S1P as immunomodulators in the prevention and treatment of autoimmune diseases and, in particular, of sarcoidosis. Because sarcoidosis presents a pathology akin to TB and autoimmune disease, prevention and treatment of sarcoidosis can be carried out according to similar methods as described in examples 1, 2 and 3 (above), using an appropriate animal model, such as the murine berylliosis model (Pfeifer et al, 1994, Int. Arch Allergy Immunol. Vol. 104, No 4:332-9) or murine listeriosis model (Mielke et al, 1997, Immunol Rev. Vol. 158, pp. 79-93).

The invention claimed is:

1. A method to treat a subject suffering from an autoimmune disease, the method comprising injecting into the subject a composition comprising sphingosine-1-phosphate (SIP) or a salt thereof, as the sole active ingredient and at a concentration from 1 to 200 microM, wherein the autoimmune disease is Crohn's disease, sarcoidosis, or inflammatory bowel disease (IBD), and wherein the concentration of the S1P is effective to reduce chronic inflammation while promoting an immune response, thereby treating the autoimmune disease.

2. The method of claim 1, wherein the autoimmune disease is Crohn's disease.

3. The method of claim 1, wherein the composition is injected simultaneously or sequentially with one or more excipients.

4. The method of claim 1, wherein the composition is a solution, emulsion, or suspension, or is microencapsulated.

5. The method of claim 1, wherein the autoimmune disease is associated with an infection caused by *Mycobacterium tuberculosis*.

6. The method of claim 1, wherein the injection is parenteral.

7. The method of claim 1, wherein the injection is into the bloodstream.

8. The method of claim 1, wherein the injection is intravenous.

9. The method of claim 1, wherein the autoimmune disease is sarcoidosis.

10. The method of claim 1, wherein the autoimmune disease is inflammatory bowel disease (IBD).

* * * * *

UNITED STATES PATENT AND TRADEMARK OFFICE
CERTIFICATE OF CORRECTION

Page 1 of 1

PATENT NO. : 10,092,643 B2
APPLICATION NO. : 11/994050
DATED : October 9, 2018
INVENTOR(S) : Marc Creus It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2204 days.

Signed and Sealed this
Tenth Day of December, 2019

Andrei Iancu
*Director of the United States Patent and Trademark Office*